(12) United States Patent
Kovach et al.

(10) Patent No.: US 6,298,252 B1
(45) Date of Patent: Oct. 2, 2001

(54) OXIMETER SENSOR WITH ENCODER CONNECTED TO DETECTOR

(75) Inventors: Dennis E. Kovach, Fremont; Michael Bernstein, San Ramon, both of CA (US)

(73) Assignee: Mallinckrodt, Inc., Hazelwood, MO (US)

( * ) Notice: Subject to any disclaimer, the term of this patent is extended or adjusted under 35 U.S.C. 154(b) by 0 days.

(21) Appl. No.: 09/401,144

(22) Filed: Sep. 22, 1999

Related U.S. Application Data

(60) Provisional application No. 60/102,314, filed on Sep. 29, 1998.

(51) Int. Cl.[7] .................................................. A61B 5/00
(52) U.S. Cl. ................................................ 600/331; 600/323
(58) Field of Search ............................ 600/336, 455, 600/310, 314, 320, 309–311, 316, 331, 322–326, 344

(56) References Cited

U.S. PATENT DOCUMENTS

| | | | |
|---|---|---|---|
| 4,781,195 | * 11/1988 | Martin | 600/336 |
| 4,800,885 | * 1/1989 | Johnson | 600/330 |
| 4,807,630 | * 2/1989 | Malinouskas | 600/323 |
| 4,846,183 | * 7/1989 | Martin | 600/336 |
| 5,086,776 | * 2/1992 | Fowler, Jr. et al. | 600/455 |
| 5,758,644 | * 6/1998 | Diab et al. | 600/323 |
| 6,198,951 | * 3/2001 | Kosuda et al. | 600/323 |

* cited by examiner

Primary Examiner—John P. Lacyk
Assistant Examiner—Matthew Kremer
(74) Attorney, Agent, or Firm—Townsend and Townsend and Crew LLP

(57) ABSTRACT

An oximeter sensor with an encoding element connected to the photodetector. The encoding element is read by reverse-biasing the photodetector, rather than using a lower voltage.

12 Claims, 3 Drawing Sheets

OXIMETER SENSOR WITH ENCODER CONNECTED TO DETECTOR

CROSS-REFERENCES TO RELATED APPLICATIONS

This application claims priority from U.S. provisional application Ser. No. 60/102,314, filed Sep. 29, 1998, having the same title, and incorporated herein by reference.

BACKGROUND OF THE INVENTION

The present invention relates to oximetry sensors and, in particular, pulse oximetry sensors which include coded information relating to characteristics of the sensor.

Pulse oximetry is typically used to measure various blood flow characteristics including, but not limited to, the blood-oxygen saturation of hemoglobin in arterial blood and heart rate of a patient. Measurement of these characteristics has been accomplished by use of a non-invasive sensor which passes light through a portion of the patient's tissue where blood perfuses the tissue, and photoelectrically senses the absorption of light in such tissue. The amount of light absorbed is then used to calculate arterial blood oxygen saturation.

The light passed through the tissue is selected to be of one or more wavelengths that are absorbed by the blood in an amount representative of the amount of the blood oxygenation. The amount of transmitted light passed through the tissue will vary in accordance with blood oxygenation. For measuring blood oxygen level, such sensors have been provided with light sources and photodetectors that are adapted to operate at two different wavelengths, in accordance with known techniques for measuring blood oxygen saturation.

An example of an encoding mechanism is shown in U.S. Pat. No. 4,700,708, incorporated herein by reference. This relates to an optical oximeter probe which uses a pair of light emitting diodes (LEDs) to direct light through blood-perfused tissue, with a detector picking up light which has not been absorbed. The operation depends upon knowing the wavelengths of the LEDs. Since the wavelengths of LEDs actually manufactured can vary, a coding resistor is placed in the sensor with the value of the resistor corresponding to the actual wavelength of at least one of the LEDs. When an oximeter is turned on, it first applies a current to the coding resistor and measures the voltage to determine the value of the resistor and thus the value of the wavelength of the LED(s) in the probe.

U.S. Pat. No. 5,259,381, incorporated herein by reference, recognizes that the coded value of the wavelength of the red LED provided by a coding resistor may be inaccurate, since the actual wavelength can vary with temperature. Accordingly, this patent teaches including a temperature sensor in the oximeter sensor to measure the actual temperature. With the actual temperature, and the coded wavelength value, a look-up table can be consulted to determine the actual LED wavelength for that temperature.

Another method of storing coded information regarding the characteristics of the LEDs is shown in U.S. Pat. No. 4,942,877, incorporated herein by reference. This patent discloses using an EPROM memory to store digital information, which can be provided in parallel or serially from the sensor probe to the remote oximeter.

Other examples of coding sensor characteristics exist in other areas. In U.S. Pat. No. 4,446,715, incorporated herein by reference, and assigned to Camino Laboratories, Inc., a number of resistors are used to provide coded information regarding the characteristics of a pressure transducer. U.S. Pat. No. 3,790,910, incorporated herein by reference, discloses another pressure transducer with a ROM storing characteristics of the individual transducer. U.S. Pat. No. 4,303,984, incorporated herein by reference, shows another sensor with digital characterization information stored in a PROM, which is read serially using a shift register.

Typically, the coding element is mounted in the sensor itself. For instance, U.S. Pat. No. 4,621,643, incorporated herein by reference, shows the coding resistor mounted in the sensor element itself. In addition, U.S. Pat. No. 5,246,003, incorporated herein by reference, shows the coding resistor being formed with a printed conductive material on the sensor itself.

In some devices, an electrical connector coupled by a cable to a device attached to a patient may include a coding element. For example, U.S. Pat. No. 3,720,199, incorporated herein by reference, shows an intra-aortic balloon catheter with a connector between the catheter and the console. The connector includes a resistor with a value chosen to reflect the volumetric displacement of the particular balloon. U.S. Pat. No. 4,684,245, incorporated herein by reference, discloses a fiberoptic catheter with a module between the fiberoptic and electrical wires connected to a processor. The module converts the light signals into electrical signals, and includes a memory storing calibration signals so the module and catheter can be disconnected from the processor and used with a different processor without requiring a recalibration.

A method for tuning the wavelength, and also providing a coded value in parallel with the LEDs, is shown in U.S. Pat. No. 5,758,644, incorporated herein by reference, and assigned to Masimo Corporation. This patent shows a way to reduce the number of leads necessary for the sensor. Claim 21 of the '644 patent also discusses a information element in parallel with the photosensing element, which is read at a predetermined voltage. Although the '644 patent does not describe how this is read for the photosensor, the reading of a coding resistor in parallel with the LED(s) is described as being done by using a lower level voltage below the shoulder of the exponential curve, as described in col. 18, lines 30–67.

SUMMARY OF THE INVENTION

The present invention is intended to overcome the disadvantages of the prior art and to provide a sensor which includes an encoding means which does not require any excessive number of extra leads, and which does not unduly interfere with an operation of sensor LEDs. The present invention provides an oximeter sensor with an encoding element connected to the photodetector. The encoding element is read by reverse-biasing the photodetector, rather than using a lower voltage.

In one embodiment, the oximeter monitor connects the lead to the photodiode to a summing junction of an operational amplifier. The summing junction is normally set to zero volts, so that the current from the photodiode due to light can be detected. A feedback resistor is connected to the operational amplifier. When an encoding resistor is placed in parallel with the photodiode, this can also be read by using the same summing junction. A test voltage is applied to the other junction of the operational amplifier to reverse bias the photodiode and to place a voltage across the calibration resistor which will then be measured by the output of the operational amplifier.

In another embodiment, the encoding element is a semiconductor chip, such as a two-lead memory chip. The chip has high impedance terminals which don't affect the normal operation of the detector.

For a further understanding of the nature and advantages of the invention, reference should be made to the following description taken in conjunction with the accompanying drawings.

DESCRIPTION OF THE SPECIFIC EMBODIMENTS

Figure 1:
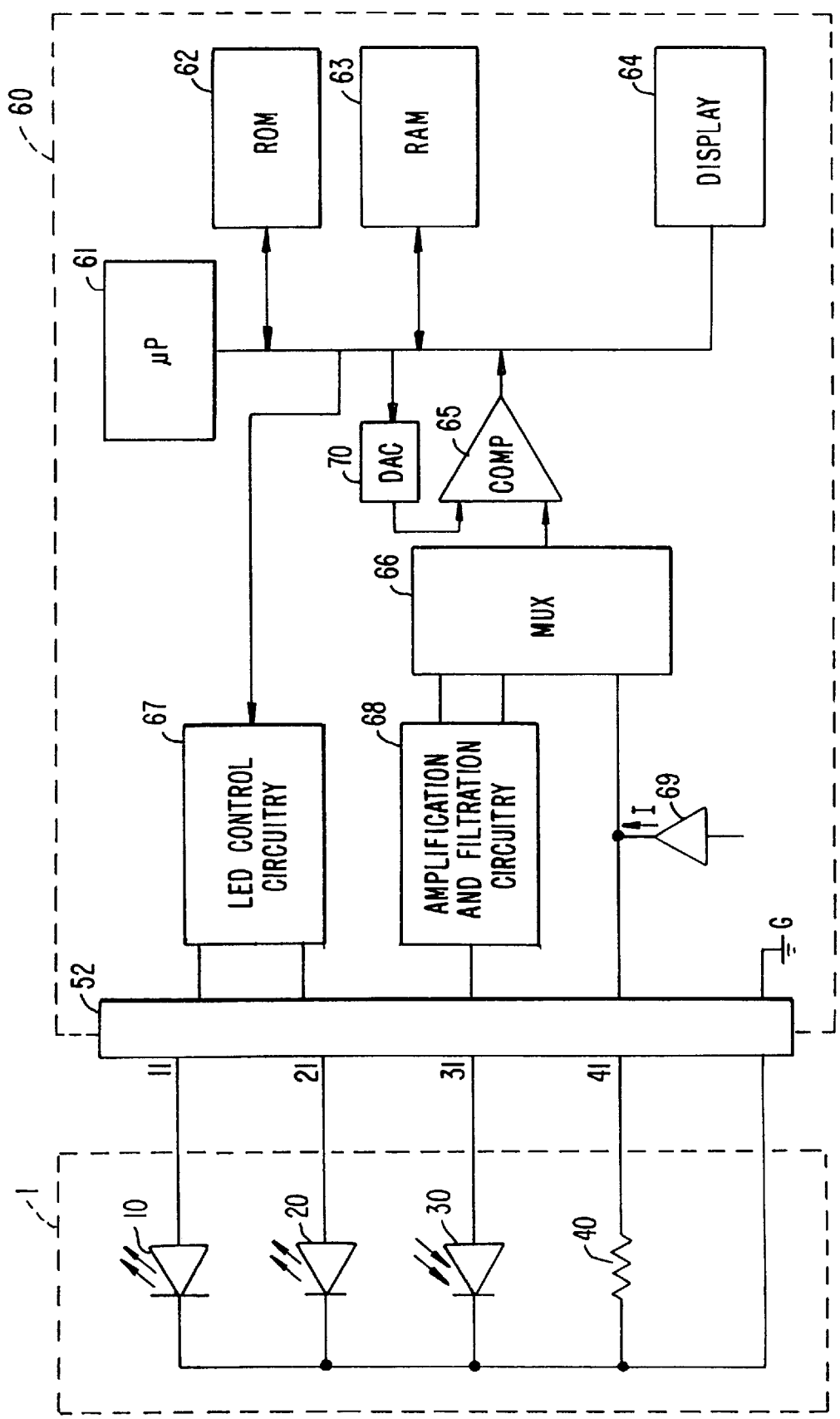
FIG. 1 is a block diagram of a prior art sensor and oximeter monitor showing a calibration resistor.

FIG. 1 shows a probe 1 which is constructed in the following manner. LED's 10, 20 are selected from batches of LEDs with generally known wavelength characteristics. The exact wavelength characteristics of the specific LED's 10, 20 chosen are determined at this time through readily available metering means. Resistor 40 or a similar impedance reference is then selected to have an impedance or specifically a resistance whose amount is exactly specified by a table made available to the factory technician for this purpose. The table relates resistance to all relevant wavelength combinations which may be expected to be encountered from the available supplies of LEDs and which significantly affect oxygen saturation calculation calibration. Oximeter 60 contains a microprocessor 61, and a read only memory 62 and random access memory 63. A table used for calibrating probe I at the factory, no matter how extensive, may be easily programmed into ROM 62 at the time oximeter 60 is fabricated. Alternatively, the ROM 62 may contain a table which correlates resistance to appropriate coefficients used for calculating saturation. Current I from current source 69 is passed through resistor 40. The resulting voltage (per Ohm's law) is passed through multiplexer 66 through comparator 65, to microprocessor 61.

Microprocessor 61 may be programmed to calculate the resistance of resistor 40 and thereafter to look up the wavelengths of LED's 10, 20 or saturation coefficients from the table in ROM 62. Microprocessor 61 is also programmed to itself recalibrate the optical comparison circuitry of oximeter 60 once the wavelengths of LEDs 10, 20 or coefficients are known.

Microprocessor 61, through LED control circuitry 67, operates LEDs 10, 20. Light from LEDs 10, 20 results in current in photodiode 30 which passes through amplification and filtration circuitry 68 to multiplexer 66. Comparator 65, and a digital to analog converter 70 are operative as an analog to digital converter means to present a digital signal to the microprocessor 61 thereby to allow the microprocessor 61 to determine oxygen saturation and/or pulse rate. Results are shown on display 64.

Figure 2:
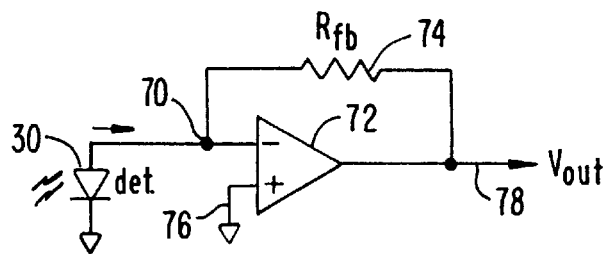
FIG. 2 is a diagram illustrating the connection of the photodiode to an operational amplifier as in the prior art.

FIG. 2 illustrates in more detail some of the elements of the amplification circuit 68 of FIG. 1. As shown in FIG. 2, photodiode 30 is connected to a summing junction 70 of an operational amplifier 72. A resistor 74 provides feedback for the operational amplifier. The other input 76 of the operational amplifier (op-amp) is connected to ground. By controlling the summing junction 70 to be at 0 volts by grounding input 76, no current should normally flow into the summing junction. Thus, any current will be that generated by detection of light by photodiode 30, which will provide current into summing junction 70, which is then amplified through resistor 74 to provide a voltage output on line 78.

Figure 3:
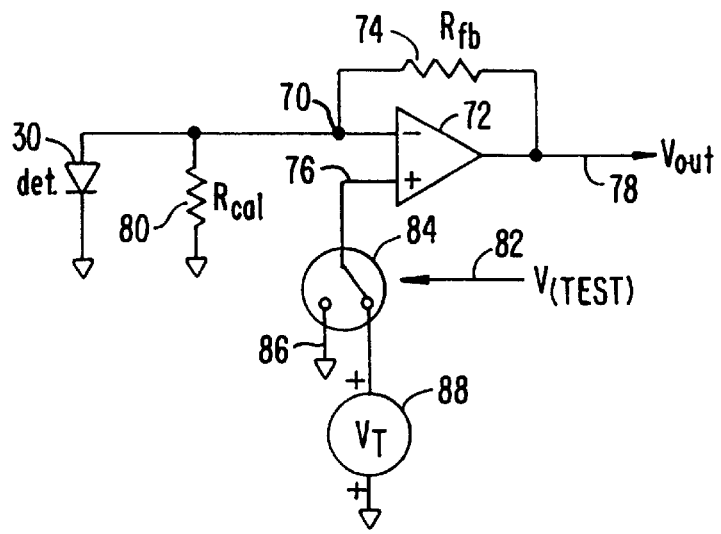
FIG. 3 is a diagram similar to FIG. 2, modified in accordance with the present invention to add a calibration resistor and test voltage source to a photodiode and operational amplifier circuit.

The present invention adds a calibration resistor 80 in parallel with photodiode 30, as shown in FIG. 3. Preferably, a calibration resistor is chosen to have a high enough resistance so that it does not interfere with photodiode 30. In normal operation, since summing junction 70 is biased at 0 volts, no current will flow through resistor 80 since both ends are at 0 volts. Because the resistance of the calibration resistor 80 has sufficiently large size, no significant current generated by photodiode 30 will pass through resistor 80, and instead the current will pass into summing junction 70.

When it is desired to measure the calibration resistor, typically on start up of the oximeter monitor with a new sensor, a control signal V(test) is applied on a control line 82 to a switch 84 connected to the second op-amp input 76. Switch 84, in normal operation, will connect input 76 to ground 86. However, upon application of the V(test) control signal, a voltage source 88 will be applied to place a negative voltage on input 76, which will also be placed on summing junction 70. This will provide a voltage across the calibration resistor 80 to allow its measurement, and will reverse bias diode 30 to ensure that it does not interfere with the measurement.

Assuming $R_{cal}$ is much greater than $R_{fb}$, an ideal op amp (no offset voltage or current included in the equations), and no allowance for reverse leakage in the photodetector, the following equations apply.

Equation 1 below shows the normal calculation of V(out) for calculating the photocurrent. Equation 2 shows the modification for calculating the calibration resistance. Equation 3 solves equation 2 for the value of the resistance.

$$V_{out} = -R_{fb} \times Photo\ Current \qquad (1)$$

$$Test\ Mode\ V_{out} = -R_{fb} \times \left(Photo\ Current + \frac{V_{test}}{R_{cal}}\right) - V_{test} \qquad (2)$$

$$R_{cal} = -R_{fb} \frac{V_{test}}{V_{out}(test) - V_{out}(normal) + V_{test}} \qquad (3)$$

As can be seen, in the test mode the voltage V(test) is applied, causing the current V(test)/Rcal to flow through Rcal resistor 80, increasing the total current to: photocurrent+V(test)/Rcal.

Figure 4:
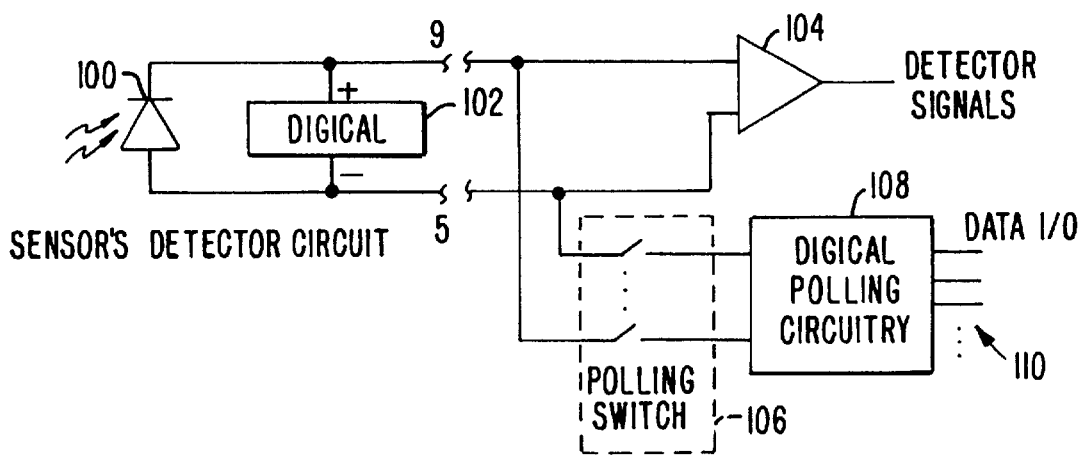
FIG. 4 is a diagram illustrating a semiconductor chip as an encoding element located across a sensor's detector leads.

FIG. 4 shows an alternate embodiment in which a sensor photodiode 100 is placed across pins 5 and 9 of a connector. A semiconductor chip 102 is the encoding element, and is mounted across pins 5 and 9 in parallel with the photodiode 100. An amplifier 104 is used to read the photodiode detector's signal. A switching circuit 106 can alternately switch the leads to a digital polling circuit 108. The data from the semiconductor chip 102 is then provided on data I/O lines 110.

Semiconductor chip 102 in one embodiment is a two-lead memory chip. The semiconductor chip is configured so that during normal pulse oximetry operation (chip 102 un-energized, photodetector 100 unbiased), the high impedance of the I/O lines of semiconductor chip 102 prevent significant photocurrent from being shunted away from the photodetector transimpedance amplifier 104. During a calibration polling period, or periodic polling periods, polling switch 106 is activated and circuit 102 is energized by either a reverse bias to the photodetector or with a varying voltage (which may be provided by polling circuit 108). This way, photodetector 100 acts only as a diode across the semiconductor chip 102.

The embodiment of FIG. 4 can either eliminate separate leads to a conventional calibration resistor, or can allow such a conventional resistor to remain unaffected and function normally with older instruments. Semiconductor chip 102 can be programmed to provide additional information to newer monitors, while older monitors could work with a resistor on a separate set of leads and at least be able to access that information.

Figure 5:
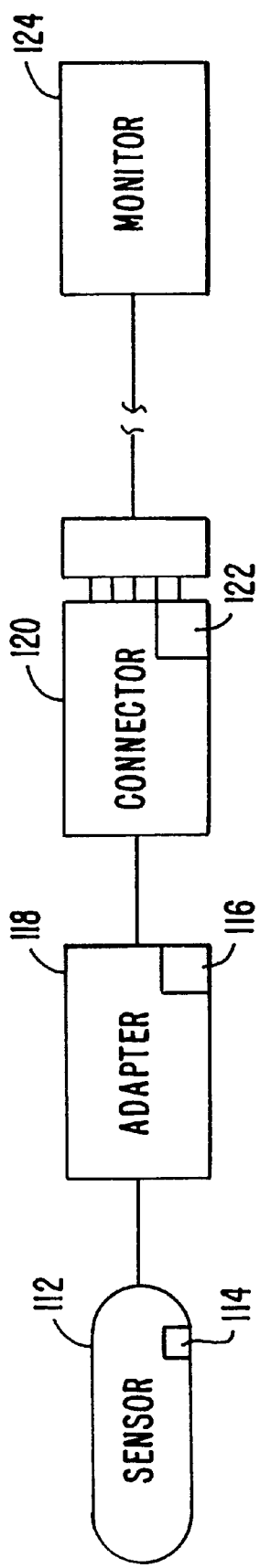
FIG. 5 is a block diagram illustrating alternate placements of the encoding element in the sensor, an adapter, or a connector.

FIG. 5 illustrates various places an encoding element, e.g., resistor 80 or semiconductor chip 102, could be placed in a system. First, a sensor 112 is shown with a semiconductor chip encoding element 114. Alternately, an encoding element 116 can be placed in an adapter 118. In yet another embodiment, a connector 120 can have an encoding element 122 attached. In any of the above locations, the encoding element can be placed across the detector leads, where it can be read by monitor 124.

As will be understood by those of skill in the art, the present invention may be embodied in other specific forms without departing from the essential characteristics thereof. For example, other elements than a resistor or semiconductor chip could be used in parallel, such as a capacitance or another diode arrangement. Alternately, a resistance or other impedance could be placed in series with the photodiode. Other arrangements will occur to those skilled in the art.

Similarly, measuring circuits other than an operational amplifier could be use to measure both the photodiode current and the calibration element. For example, a switch could switch in a fixed current source to measure the calibration resistor, and otherwise connect a current measuring circuit to the photodiode, such as a transimpedance amplifier.

In alternate embodiments, the encoding element can be a capacitor, or a resistor and a zener diode, or a resonant circuit of a capacitor and an inductor. These elements can be mounted in parallel with the photodetector. Alternately, a photodetector with a chosen reversed biased zener voltage could be used, with the reversed biased voltage being measured to provide the encoding value. Alternately, another element or photodetector with a controlled reverse breakdown could be used. The measuring circuit in the monitor can measure a capacitor or resonant circuit by dynamically applying a voltage and measuring the current in response. This allows determination of the capacitor value or the resonant frequency.

Figure 6C:
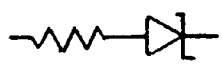
FIGS. 6A–6C are diagrams of alternate embodiments of the encoding element of the invention.
Figure 6B:
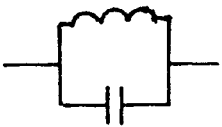
Figure 6A:
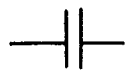

FIGS. 6A–6C are diagrams of alternate embodiments of the encoding element of the invention. The encoding elements of FIGS. 6A–6C are placed in parallel with the photodetector.

Accordingly, the foregoing description is intended to be illustrative, but not limiting, of the scope of the invention which is set forth in the following claims.

What is claimed is:

1. An oximeter monitor comprising:
    a drive circuit configured to provide drive current to a light emitter in an oximeter sensor;
    a detector circuit coupled to a detector lead for connecting to a light detector in said oximeter sensor; and
    a measuring circuit, coupled to said detector lead, for receiving information from an encoding element connected to said detector lead in said oximeter sensor, the encoding element encoding a characteristic of the sensor, said measuring circuit including a circuit for reverse biasing a photodiode connected to said detector lead.

2. The oximeter monitor of claim 1 wherein said measuring circuit comprises a circuit for measuring a voltage across a resistor.

3. The oximeter monitor of claim 2 wherein:
    said measuring circuit includes an operational amplifier, wherein said detector lead is connected to a summing junction of said operational amplifier; and
    said measuring circuit further includes a test voltage selectively coupled to another junction of said operational amplifier.

4. The oximeter monitor of claim 1 further comprising:
    a switch coupled between said detector circuit and said measuring circuit.

5. The oximeter monitor of claim 1 wherein said measuring circuit is configured to determine a reverse biased zener voltage of said light detector.

6. The oximeter monitor of claim 1 wherein said measurement circuit is configured to dynamically measure a current response to an applied voltage.

7. An oximeter system comprising:
    (a) an oximeter sensor having
        a light emitter for emitting light having a limited wavelength spectrum,
        a light detector mounted in said sensor to detect light of said wavelength spectrum,
        an encoding element coupled to said light detector, said encoding element providing information corresponding to said limited wavelength spectrum; and
    (b) an oximeter monitor having
        a drive circuit configured to provide drive current to said light emitter,
        a detector circuit coupled to a detector lead for connecting to said light detector, and
        a measuring circuit, coupled to said detector lead, for receiving said information from said encoding element, said measuring circuit including a circuit for reverse biasing said light detector.

8. The oximeter system of claim 7 wherein
    said encoding element comprises a resistor; and
    said light detector comprises a photodiode.

9. The oximeter system of claim 7 wherein said information corresponding to said limited wavelength spectrum provided by said encoding element further comprises information indicative of a wavelength of the light such that appropriate coefficients can be chosen for calculating oxygen saturation of the patient.

10. The oximeter system claim 7 wherein said information corresponding to said limited wavelength spectrum provided by said encoding element further comprises either a manufacturer of the sensor or a sensor model.

11. The oximeter system of claim 7 wherein said encoding element is connected in parallel with said light detector.

12. The oximeter system of claim 7 wherein said encoding element is
    either a resistor, a semiconductor memory chip, a two lead memory chip, a capacitor, a resonant circuit comprising a capacitor and an inductor, a resistor and a zener diode, or a controlled reverse breakdown of said light detector.

* * * * *